United States Patent [19]
Austin-Phillips et al.

[11] Patent Number: 5,981,835
[45] Date of Patent: Nov. 9, 1999

[54] TRANSGENIC PLANTS AS AN ALTERNATIVE SOURCE OF LIGNOCELLULOSIC-DEGRADING ENZYMES

[75] Inventors: Sandra Austin-Phillips; Richard R. Burgess, both of Madison; Thomas L. German, Hollandale; Thomas Ziegelhoffer, Madison, all of Wis.

[73] Assignee: Wisconsin Alumni Research Foundation, Madison, Wis.

[21] Appl. No.: 08/883,495

[22] Filed: Jun. 26, 1997

Related U.S. Application Data

[60] Provisional application No. 60/028,718, Oct. 17, 1996.
[51] Int. Cl.$^6$ .............................. C12N 15/82; C12N 5/04; A01H 5/00
[52] U.S. Cl. .................... 800/278; 536/23.1; 536/23.74; 435/69.1; 435/70.1; 435/468; 435/469; 435/410; 435/414; 800/278; 800/284; 800/317.3
[58] Field of Search ............................... 536/23.74, 23.1; 800/205, DIG. 24, DIG. 43, 278, 284, 317.3; 435/69.1, 70.1, 468, 469, 410, 414

[56] References Cited

U.S. PATENT DOCUMENTS

| | | |
|---|---|---|
| 5,432,074 | 7/1995 | Evans et al. . |
| 5,457,046 | 10/1995 | Wöldike et al. . |
| 5,529,919 | 6/1996 | Knowles et al. . |

FOREIGN PATENT DOCUMENTS

| | | |
|---|---|---|
| WO 87/00865 | 2/1987 | WIPO . |
| WO 94/26880 | 11/1994 | WIPO . |
| WO 94/29460 | 12/1994 | WIPO . |

OTHER PUBLICATIONS

Adney et al. (1994), Cellulase assays. In: *Enzymatic conversion of biomass for fuels production*, Eds. M. E. Himmel, J.O. Baker & R.P. Overend. ACS symposium series 566.

Aspegren et al. (1995), Secretion of a heat–stable fungal β–glucanase from transgenic, suspension–cultured barley cells. *Molecular Breeding* 1:91–99.

Baker et al. (1992), Thermal denaturation of *T. reesei* cellulases studied by differential scanning calorimetry and tryptophan fluorescene. *Apply. Biochem. Biophys.* 34:217–231.

Bednarek (1991), The barley lectin carboxy–terminal peptide is a vacuolar protein sorting determinant in plants. *The Plant Cell* 3:1195–1206.

Belkacemi et al. (1996), Enzymatic hydrolysis of timothy grass pretreated by ammonia fiber explosion. In: *Liquid fuels and industrial products from renewable resources, Proceedings of the third liquid fuel conference*, Eds. J.S. Cundiff, E.E. Gavett, C. Hansen, C. Peterson, M.A. Sanderson, H. Shapouri & D.L. VanDyne. ASAE publication 08–96 pp. 232–240.

Bingham et al. (1975), Breeding alfalfa which regenerates from callus tissue in culture. *Crop Sci.* 15:719–721.

Brown and Atanassov (1985), Role of genetic background in somatic embryogenesis in Medicago. *Plant Cell Tissue Organ Culture* 4:107–114.

Carrer et al. (1993), Kanamycin resistance as a selectable marker for plastid transformation in tobacco. *Mol. Gen. Genet.* 241:49–56.

Castillo et al. (1994), Rapid production of fertile transgenic plants of Rye. *Bio/Technology* 12:1366–1371.

Comai et al. (1990), Novel and useful properties of a chimeric plant promoter combining CaMV 35S and MAS elements. *Plant Mol. Biol.* 15:373–381.

Coughlan, M.P. (1988), Staining Techniques for the Detection of the Individual Components of Cellulolytic Enzyme Systems. *Methods in Enzymology* 160:135–144.

de Castro Silva Filho et al. (1996), Mitochondrial and chloroplast targeting sequences in tandem modify protein import specificity in plant organelles. *Plant Mol. Biol.* 30:769–780.

Divne et al. (1994), The three–dimensional crystal structure of the catalytic core of cellobiohydrolase I from *Trichoderma reesei. Science* 265:524–528.

Ghangas & Wilson (1988), Cloning of the *Thermomonospora fusca* endoglucanase E2 gene in *Streptomyces lividans*: Affinity purification and functional domains of the cloned gene product. *Appl. Envir. Microbiol.* 54:2521–2526.

Grohmann et al. (1992), Potential for fuels from biomass and wastes. In: *Emerging technologies for materials and chemicals from biomass*, Eds. R.M. Powell, T.P. Schultz and R. Narayan. ACS symposium series 576.

Henrissat et al. (1995), Synergism of cellulases from *Trichoderma reesei* in the degradation of cellulose. *Bio/Technology* 3:722–726.

Horsh et al. (1985), A simple and general method for transferring genes into plants. *Science* 227:1229–1231.

Irwin et al. (1993), Activity studies of eight purified cellulases: Specificity, synergism, and binding domain effects. *Biotechnol. Bioeng.* 42:1002–1013.

Ishida et al. (1996), High efficiency transformation of maize mediated by *Agrobacterium tumefaciens. Nature Biotechnology* 14:745–750.

Keegstra et al. (1993), Targeting of proteins into chloroplasts. *Physiologia Plantarum* 93:157–162.

Lao et al. (1991), *J. Bacteriol.* 173:3397–3407.

Mason et al. (1988), Proteins homologous to leaf glycoproteins are abundant in stems of dark–grown soy bean seedlings. Analysis of proteins and cDNAs. *Plant Mol. Biol.* 11:845–856.

McBride and Summerfelt (1990), Improved binary vectors for Agrobacterium mediated plant transformation. *Plant Mol. Biol.* 14:269–276.

(List continued on next page.)

*Primary Examiner*—Gary Benzion
*Assistant Examiner*—Ousama Zaghmout
*Attorney, Agent, or Firm*—DeWitt Ross & Stevens S. C.

[57] ABSTRACT

Transgenic plants which express cellulose-degrading enzymes, methods to make the transgenic plants, and methods to use the cellulose-degrading enzymes produced by the transgenic plants are disclosed.

17 Claims, 4 Drawing Sheets

OTHER PUBLICATIONS

McBride et al. (1994), Controlled expression of plastid transgenes in plants based on a nuclear DNA–encoded and plastid–targeted T7 RNA polymerase. *Proc. Natl. Acad. Sci. USA* 91:7301–7305.

Micelli et al. (1996), Integrated treatments of steam explosion and enzymatic hydrolysis to produce energetic and industrial products from lignocellulosic biomasses. *Agro–food–Industry Hi–tech* 7:25–28.

Murashige and Skoog (1962), A revised medium for rapid growth and bioassays with tobacco tissue cultures. *Physiol. Plant* 15:473–497.

Pentilla et al. (1987), *Yeast* 3:175–185.

Sonnewald et. al. (1991), Transgenic tobacco plants expressing yeast–derived invertase in either the cytosol, vacuole or apoplast: a powerful tool for studying sucrose metabolism and sink/source interactions. *The Plant J.* 1:95–106.

Spezio et al. (1993), Crystal structure of the catalytic domain of a thermophilic endocellulase. *Biochemistry* 32:9906–9916.

Tucker et al. (1989), Ultra–thermostable cellulases from *Acidothermus cellulolyticus* comparison of temperature optima with previously reported cellulases. *Biotechnology* 7:817–820.

Vasil et al. (1993), Rapid production of transgenic wheat plants by direct particle bombardment of cultured immature embyros. *Bio/Technology* 11:1553–1558.

Wandelt et al. (1992), Vicilin with carboxy–terminal KDEL is retained in the endoplasmic reticulum and accumulates to high levels in the leaves of transgenic plants. *Plant J.* 2:181–192.

Zambryski, P., J. Tempe, and J. Schell (1989), Transfer and function of T–DNA genes from Agrobacterium Ti and Ri plasmids in plants. *Cell* 56:193–201.

Zhang et al. (1995), Characterization of a *Thermomonospora fusca* exocellulase. *Biochemistry* 34:3386–3395.

Xu et al. FEBS Letters. 1994. vol. 348: 206–210.

Napoli et al. The Plant Cell. 1989. vol. 2: 278–289.

Carvalho et al. The EMBO Journal. 1992. vol. 11: 2595–2602.

Somero, George N., Proteins and Temperature, *Annu. Rev. Physiol.* (1995), 57:43–68.

Jacobs et al., Post–transcriptional β–1,3–glucanase gene silencing involves increased transcript turnover that is translation–independent, *The Plant Journal* (1977), 12(4):885–893.

Davies et al., Genetics of homology–dependent gene silencing in Arabidopsis; a role for methylation, The Plant Journal (1997), 12(4): 791–804.

De Loose et al., Primary structure of a homonally egulated β–glucanase of *Nicotiana plumbaginifolia*, Gene (1988), 70:13–23.

Castresana et al., Tissue–Specific and Pathogen–Induced Regulation of a *Nicotiana plumbaginifolia* β–1,3–Glucanase Gene, *The Plant Cell* (1990), 2:1131–1143.

Smyth, David R., Gene silencing: Cosuppression at a distance, *Current Biology* (1997), vol. 7, No. 12, R793–R795.

Meyer, Peter, Understanding and controlling transgene expression, *Tibtech* (Sep. 1995), 13:332–337.

TRANSGENIC PLANTS AS AN ALTERNATIVE SOURCE OF LIGNOCELLULOSIC-DEGRADING ENZYMES

Priority is claimed to provisional application serial No. 60/028,718, filed Oct. 17, 1996.

This invention was made with United States government support awarded by the following agencies:
DOE Grant No. DE-FC05-92OR22072;
DOE Grant No. DE-FC05-92OR22072 (via CPBR, Ref. No. OR22072-34;
USDA Grant Nos. 94-34190-1204 and 92-34190-6941 (via Purdue, Award Nos. 5930120-28 and 5930213-17).

The United States has certain rights in this invention.

FIELD OF THE INVENTION

The present invention is directed to the production of cellulose-degrading enzymes in genetically recombinant plants and the recombinant plants themselves.

BIBLIOGRAPHY

Complete bibliographic citations for the non-patent references discussed hereinbelow are included in the Bibliography section, immediately preceding the claims. All of the references cited below are incorporated herein by reference.

DESCRIPTION OF THE PRIOR ART

Lignocellulosic plant matter, such as agricultural and forestry waste, as well as energy crops produced specifically for biomass, offer tremendous potential for the renewable production of fuel and as chemical feedstocks. However, production cost for desired products such as alcohols from lignocellulosic material is significantly higher than the production cost of equivalent alternatives. However, the prospect, either real or perceived, of limited fossil fuel reserves, along with the geo-political issues which swirl about petroleum-producing countries and regions, renders the production of basic chemical feedstocks and fuels from local, renewable sources an attractive alternative to fossil fuels.

For instance, alcohols have the potential to be excellent alternative transportation fuels if their production costs can be lowered. Brazil has sponsored several programs to replace car engines which run on gasoline alone to engines which run on ethanol or a gasoline-ethanol mix.

Unfortunately, the production of ethanol and other feedstock chemicals from lignocellulosic material is far more complex than an analogous production utilizing a starch-based starting material. Compared to lignocellulosic materials, starch is a simple polymer which is readily hydrolyzed to glucose. Yeasts can then be used to convert the glucose to ethanol.

In contrast, lignocellulosic biomass is a much more complex substrate in which crystalline cellulose is embedded within a matrix of hemicellulose and lignin. The intricate structure and relative inaccessibility of these substrates requires pre-treatment for the disruption of the lignocellulosic material, as well as hydrolysis of hemicellulose and lignin into xylose and phenolic compounds, respectively. (See, for instance, Micelli et al. (1996), Belkacemi et al. (1996), and Grohmann et al. (1992).)

Several enzymes which degrade lignocellulosic material, commonly referred to as "cellulases," are known. The term "cellulase" shall be used herein to refer to any and all enzymes which catalyze the cleavage of cellulosic or lignocellulosic materials. Explicitly, but not exclusively, included within this definition are those cellulases which fall under the Enzyme Classification heading EC 3.2.1.x. Various genes encoding cellulases have also been isolated and characterized.

For instance, genes which encode endoglucanases from the fungus *Trichoderma reesei* are known and have been successfully incorporated and expressed in yeast. See, for instance, Pentilla et al. (1987). Likewise, cellulase E2 (EC 3.2.1.4) and cellulase E3 (EC 3.2.1.91) from the thermotolerant bacterium *Thermomonospora fusca* are known. See Lao et al. (1991), Spezio et al. (1993) and Zhang et al. (1995).

From a functional viewpoint, cellulases are catagorized into two large sub-groups based upon whether they catalyze cleavage from the cellulose chain ends (exocellulases) or if they catalyze cleavage in the middle of the cellulose chain (endocellulases). For instance, cellobiohydrolase I of *T. reesei* (CBH I, EC 3.2.1.91) is an exocellulase, which degrades crystalline cellulose by cleavage from the chain ends. By way of further illustration, CBH I is a 68 kDa protein with a two-domain architecture which is shared by many cellulases. In this chemical architecture, a large catalytic domain is joined to a cellulose-binding domain (CBD) through a flexible linker region. See Divne et al. (1994). Similarly, cellulase E3 of *T. fusca* is also an exocellulase.

Different types of cellulases exhibit synergistic activity on complex substrates. This synergism, especially between exocellulases, is believed to be due to differences in their patterns of absorption to and hydrolysis of complex cellulose substrates. See Henrissat et al. (1995).

Illustratively, cellulase E2 of *T. fusca* is a 40 kDa endocellulase which cleaves the cellulose chain internally. Such cleavage generates more chain ends for attack by exocellulases. Consequently when CBH I, E2, and E3 cellulases are combined, their activity together is approximately 5-fold greater than their additive individual activities. (See, for instance, Irwin et al. (1993) and WO 94/26880.) It is important to note that proteolytic fragments of cellulases can substitute for the intact enzymes in synergistic mixtures. For example, when combined with *T. fusca* E3 and CBH I, the catalytic domain of *T. fusca* E2 ("E2cd") is as active as the intact enzyme in the digestion of filter paper substrate, Irwin et al. (1993).

A wide range of compositions containing cellulases are described in the patent literature. For instance, Evans et al., U.S. Pat. No. 5,432,074, describe the use of a formulation consisting essentially of a combination of xylanase and xylosidase, but being essentially free of glucanase and cellobiohydrolase. The formulation also contains a lactic acid-producing bacteria. The formulation is used to treat silage to increase its nutritive value. In operation, the action of the xylanase and xylosidase enzymes degrades non-cellulosic polysaccharides found in the silage material thereby producing sugars for fermentation.

Heterodimers of different types of cellulose-degrading enzymes are described in WO 94/29460. Here, a β-glucosidase molecule and a cellobiohydrolase molecule (i.e., an exocellulase) are chemically bonded to one another by a crosslinking reagent to yield a single molecule which retains the enzymatic activities of the two separate molecules.

Expression constructs which contain cellulase genes for the transformation of yeast have been constructed. For example, Knowles et al., U.S. Pat. No. 5,529,919, describe the transformation of *S. cerevisiae* to contain and express a thermostable β-endoglucanase (EG I) of *T. reesei*.

Likewise, attempts have been made to produce transgenic plants which express cellulose-degrading enzymes. Aspegren et al. (1995) describe transgenic suspension-cultured barley cells which express EG I of *T. reesei*. The cells were transformed by particle bombardment and transformed cells selected by a co-transformed antibiotic resistance marker. However, no attempt was made to regenerate complete plants from the cultured cells. Of particular note, this reference states that the production of β-glucanases in plant cells may be hampered by the fact that these enzymes catalyze the hydrolysis of essential cell wall components. Attempts by these authors to stably transform tobacco cells with the same construct used to successfully transform the suspended barley cells failed. Here, the authors observed that after transient expression in tobacco protoplasts, cell wall synthesis never resumed.

SUMMARY OF THE INVENTION

The present invention is drawn to genetically recombinant plants which contain one or more exogenous gene sequences which encode one or more cellulose-degrading gene products. The gene product or products are expressed in recoverable quantities in the recombinant plants and can be isolated from the plants, if desired. In the preferred embodiment, the genetically recombinant plant expresses the gene product constituitively.

However, the invention also encompasses recombinant plants which express the gene product stage-specifically or tissue-specifically. For example, the gene product or products can be expressed in a plant tissue such as the seeds, fruit, leaves, or tubers of the transformed plant host.

The invention is further drawn to recombinant plants as noted above, wherein the plant contains two exogenous genes whose respective gene products are expressed independently of one another. This allows for different types of cellulases to be expressed in different locations within the same recombinant plant. For example, the plant host can be transformed to express two or more heterologous cellulases in different sub-cellular compartments such as the plastid, cytosol, endoplasmic reticulum, mitochondrion, inclusion body, or vacuole. In addition, chloroplast targeting can also be accomplished through the use of direct chloroplast transformation, an approach that circumvents many of the problems associated with expression of heterologous genes in the nuclear genome. Carrer et al. (1993), McBride et al. (1994).

The invention is further drawn to a method for producing cellulose-degrading enzymes. The method comprises transforming a plant host with one or more exogenous genes which encode one or more cellulose-degrading gene products such that the gene product or products are expressed in recoverable quantities. The plant matter containing the expressed protein can be used directly as a feedstock for biomass conversion, or, if desired, the exogenous enzymes so produced can be isolated and purified.

The cellulases produced by the transgenic plants of the present invention can be utilized in the same manner as conventionally-derived cellulases. For instance, cellulases produced by the transgenic plants of the present invention can be isolated and used in fermentation processes such as brewing and wine-making. Here, the cellulases function to hydrolyze cellulose and β-glucans during fermentation. Or, as described in Example 4, below, whole plants transformed to express cellulases can be used directly or added to ensiled plant matter to increase the extent of fermentation of the ensiled matter. Plants transformed to express functional cellulases may also be fed directly to livestock, where the cellulase activity aids in the digestion of lignocellulosic substrates.

Cellulases produced in the transgenic plants of the present invention can also be utilized in the production of ethanol and other feedstock chemicals from lignocellulosic substrates.

Cellulases produced by transgenic plants of the present invention can also be used in the textile, pulping, and paper-making industries. For instance, cellulases are conventionally used to treat denim fabrics to give them a "stone-washed" appearance. Cellulases are also used to modify paper pulps by digesting the cellulose fibers contained within the pulp. The cellulases produced by the transgenic plants described herein can be used in this fashion.

DETAILED DESCRIPTION OF THE INVENTION

The invention is directed to genetically recombinant plants which express one or more exogenous cellulose-degrading (cellulase) enzymes. The invention is further drawn to a method of producing cellulases in plants. The invention allows the production of cellulases using the means and methods of large-scale agriculture rather than the conventional route of large-scale fermentation of the bacteria or fungi which are native producers of the cellulases.

The recombinant plants are produced by incorporating into a plant host genome one or more expression constructs comprising a DNA sequence which encodes a protein having cellulose-degrading activity. Introduction of the exogenous gene or genes into the plant is accomplished by any means known to the art. The expression constructs described hereinbelow enable the stable transformation of plants with one or more genes which encode cellulose-degrading enzymes. The constructs include a DNA coding sequence which encodes a cellulase (as that term is described herein) which is operatively linked to regulatory sequences which direct constituitive, stage-specific, or tissue-specific expression of the cellulase DNA.

Cellulose-Degrading Enzymes (Cellulases) and Genes:

As noted above, the term "cellulase" shall be used herein to refer to any and all enzymes which catalyze the cleavage of cellulosic or lignocellulosic materials. As used herein, "cellulase" is synonymous with "cellulose-degrading enzymes." Explicitly, but not exclusively, included within the term cellulases are those enzymes which fall under the Enzyme Classification heading EC 3.2.1.x. A non-exhaustive list of these enzymes, the genes for all of which can be used in the present invention, includes the following:

Table 1: Polysaccharide-Degrading Enzymes

EC 3.2.1.1 (Alpha-amylase)
EC 3.2.1.2 (Beta-amylase)
EC 3.2.1.3 (Glucan 1,4-alpha-glucosidase)
EC 3.2.1.4 (Cellulase, also known as beta-1,4-endoglucanase, e.g., cellulase E2)
EC 3.2.1.6 (Endo-1,3(4)-beta-glucanase)
EC 3.2.1.7 (Inulinase)
EC 3.2.1.8 (Endo-1,4-beta-xylanase)
EC 3.2.1.10 (Oligo-1,6-glucosidase)
EC 3.2.1.11 (Dextranase)
EC 3.2.1.14 (Chitinase)
EC 3.2.1.15 (Polygalacturonase)
EC 3.2.1.17 (Lysozyme)
EC 3.2.1.18 (Exo-alpha-sialidase)
EC 3.2.1.20 (Alpha-glucosidase)
EC 3.2.1.21 (Beta-glucosidase)
EC 3.2.1.22 (Alpha-galactosidase)
EC 3.2.1.23 (Beta-galactosidase)
EC 3.2.1.24 (Alpha-mannosidase)
EC 3.2.1.25 (Beta-mannosidase)
EC 3.2.1.26 (Beta-fructofuranosidase)
EC 3.2.1.28 (Alpha,alpha-trehalase)
EC 3.2.1.31 (Beta-glucuronidase)
EC 3.2.1.32 (Xylan endo-1,3-beta-xylosidase)
EC 3.2.1.33 (Amylo-1,6-glucosidase)
EC 3.2.1.35 (Hyaluronoglucosminidase)
EC 3.2.1.36 (Hyaluronoglucuronidase)
EC 3.2.1.37 (Xylan 1,4-beta-xylosidase)
EC 3.2.1.38 (Beta-D-fucosidase)
EC 3.2.1.39 (Glucan endo-1,3-beta-D-glucosidase)
EC 3.2.1.40 (Alpha-1-rhamnosidase)
EC 3.2.1.41 (Alpha-dextrin endo-1,6-alpha-glucosidase)
EC 3.2.1.42 (GDP-glucosidase)
EC 3.2.1.43 (Beta-L-rhamnosidase)
EC 3.2.1.44 (Fucoidanase)
EC 3.2.1.45 (Glucosylceramidase)
EC 3.2.1.46 (Galactosylceramidase)
EC 3.2.1.47 (Galactosylgalactosylglucosylceramidase)
EC 3.2.1.48 (Sucrose alpha-glucosidase)
EC 3.2.1.49 (Alpha-N-acetylgalactosaminidase)
EC 3.2.1.50 (Alpha-N-acetylglucosaminidase)
EC 3.2.1.51 (Alpha-L-fucosidase)
EC 3.2.1.52 (Beta-N-acetylhexosaminidase)
EC 3.2.1.53 (Beta-N-acetylgalactosaminidase)
EC 3.2.1.54 (Cyclomaltodextrinase)
EC 3.2.1.55 (Alpha-N-arabinofuranosidase)
EC 3.2.1.56 (Glucuronosyl-disulfoglucosamine glucuronidase)
EC 3.2.1.57 (Isopullulanase)
EC 3.2.1.58 (Glucan 1,3-beta-glucosidase)
EC 3.2.1.59 (Glucan endo-1,3-alpha-glucosidase)
EC 3.2.1.60 (Glucan 1,4-alpha-maltotetrahydrolase)
EC 3.2.1.61 (Mycodextranase)
EC 3.2.1.62 (Glycosylceramidase)
EC 3.2.1.63 (1,2-Alpha-L-fucosidase)
EC 3.2.1.64 (2,6-Beta-fructan 6-levanbiohydrolase)
EC 3.2.1.65 (Levanase)
EC 3.2.1.66 (Quercitrinase)
EC 3.2.1.67 (Galacturan 1,4-alpha-galacturonidase)
EC 3.2.1.68 (Isoamylase)
EC 3.2.1.70 (Glucan 1,6-alpha-glucosidase)
EC 3.2.1.71 (Glucan endo-1,2-beta-glucosidase)
EC 3.2.1.72 (Xylan 1,3-beta-xylosidase)
EC 3.2.1.73 (Licheninase)
EC 3.2.1.74 (Glucan 1,4-beta-glucosidase)
EC 3.2.1.75 (Glucan endo-1,6-beta-glucosidase)
EC 3.2.1.76 (L-iduronidase)
EC 3.2.1.77 (Mannan 1,2-(1,3)-alpha-mannosidase)
EC 3.2.1.78 (Mannan endo-1,4-beta-mannosidase)
EC 3.2.1.80 (Fructan beta-fructosidase)
EC 3.2.1.81 (Agarase)
EC 3.2.1.82 (Exo-poly-alpha-galacturonosidase)
EC 3.2.1.83 (Kappa-carrageenase)
EC 3.2.1.84 (Glucan 1,3-alpha-glucosidase)
EC 3.2.1.85 (6-Phospho-beta-galactosidase)
EC 3.2.1.86 (6-Phospho-beta-glucosidase)
EC 3.2.1.87 (Capsular-polysaccharide endo-1,3-alpha-galactosidase)
EC 3.2.1.88 (Beta-L-arabinosidase)
EC 3.2.1.89 (Arabinogalactan endo-1,4-beta-galactosidase)
EC 3.2.1.90 (Arabinogalactan endo-1,3-beta-galactosidase)
EC 3.2.1.91 (Cellulose 1,4-beta-cellobiosidase, also known as beta-1,4-exocellulases; cellobiohydrolases; and exo-glucanases; e.g., cellulase E3, CBH I)
EC 3.2.1.92 (Peptidoglycan beta-N-acetylmuramidase)
EC 3.2.1.93 (Alpha,alpha-phosphotrehalase)
EC 3.2.1.94 (Glucan 1,6-alpha-isomaltosidase)
EC 3.2.1.95 (Dextran 1,6-alpha-isomaltotriosidase)
EC 3.2.1.96 (Mannosyl-glycoprotein endo-beta-N-acetylglucosamidase)
EC 3.2.1.97 (Glycopeptide alpha-N-acetylgalactosaminidase)
EC 3.2.1.98 (Glucan 1,4-alpha-maltohexaosidase)
EC 3.2.1.99 (Arabinan endo-1,5-alpha-L-arabinosidase)
EC 3.2.1.100 (Mannan 1,4-beta-mannobiosidase)
EC 3.2.1.101 (Mannan endo-1,6-beta-mannosidase)
EC 3.2.1.102 (Blood-group-substance endo-1,4-beta-galactosidase)
EC 3.2.1.103 (Keratan-sulfate endo-1,4-beta-galactosidase)
EC 3.2.1.104 (Steryl-beta-glucosidase)
EC 3.2.1.105 (Strictosidin beta-glucosidase)
EC 3.2.1.106 (Mannosyl-oligosaccharide glucosidase)
EC 3.2.1.107 (Protein-glucosylgalactosylhydroxylysine glucosidase)
EC 3.2.1.108 (Lactase)
EC 3.2.1.109 (Endogalactosaminidase)
EC 3.2.1.111 (Mucinaminylserine mucinaminidase)
EC 3.2.1.111 (1,3-Alpha-L-fucosidase)
EC 3.2.1.112 (Deoxglucosidase)
EC 3.2.1.113 (Mannosyl-oligosaccharide 1,2-alpha-mannosidase)
EC 3.2.1.114 (Mannosyl-oligosaccharide 1,3-1,6-alpha-mannosidase)
EC 3.2.1.115 (Branched-dextran exo-1,2-alpha-glucosidase)
EC 3.2.1.116 (Glucan 1,4-alpha-maltotriohydrolase)
EC 3.2.1.117 (Amygdalin beta-glucosidase)

EC 3.2.1.118 (Prunasin beta-glucosidase)
EC 3.2.1.119 (Vicianin beta-glucosidase)
EC 3.2.1.120 (Oligoxyloglucan beta-glycosidase)
EC 3.2.1.121 (Polymannuronate hydrolase)
EC 3.2.1.122 (Maltose-6'-phosphate glucosidase)
EC 3.2.1.123 (Endoglycosylceramidase)
EC 3.2.1.124 (3-Deoxy-2-octulosonidase)
EC 3.2.1.125 (Raucaffricine beta-glucosidase)
EC 3.2.1.126 (Coniferin beta-glucosidase)
EC 3.2.1.122 (1,6-Alpha-L-fucosidase)
EC 3.2.1.128 (Glycyrrhizinate beta-glucuroniidase)
EC 3.2.1.129 (Endo-alpha-sialidase)
EC 3.2.1.130 (Glycoprotein endo-alpha-1,2-mannosidase)
EC 3.2.1.131 (Xylan alpha-1,2-glucuronosidase)
EC 3.2.1.132 (Chitosanase)
EC 3.2.1.133 (Glucan 1,4-alpha-maltohydrolase)
EC 3.2.1.134 (Difructose-anhydride synthase)
EC 3.2.1.135 (Neopullulanase)
EC 3.2.1.136 (Glucuronoarabinoxylan endo-1,4-beta-xylanase)
EC 3.2.1.137 (Mannan exo-1,2-1,6-alpha-mannosidase)
EC 3.2.1.138 (Anhydrosialidase)

DNA sequences encoding enzymes having any of the above-described functionalities can be obtained from several microbial sources, including bacterial and fungal sources. Cloning the gene or cDNA sequence of the desired enzyme can be achieved by several well-known methods. A preferred method is to purify the cellulase of interest (or purchase a sample if commercially available) and determine its N-terminal amino acid sequence, as well as several internal amino acid sequences, using known methods. Oligonucleotide probes corresponding to the amino acid sequence are then constructed (again using known methods) and used to screen a genomic or cDNA library of the organism from which the cellulase was isolated. Positive hybrids are identified, characterized using known methods (restriction enzyme analysis, etc.), and cloned by known means to yield DNA fragments containing the coding sequence for the desired cellulase activity. (See, for instance, *Current Protocols in Molecular Biology*, Chapters 5 and 6.)

If a partial nucleotide sequence of the cellulase of choice is already known, this information can be used to construct suitable primers to directly clone the corresponding cDNA using the polymerase chain reaction (PCR). (See *Current Protocols in Molecular Biology*, Chapter 15.)

Particularly preferred for use in the present invention are those enzymes falling within the classifications EC 3.2.1.4; EC 3.2.1.6; EC 3.2.1.21; and EC 3.2.1.91. The functionality of these particular enzymes is summarized as follows:

EC 3.2.1.4 enzymes (β-1,4-endoglucanases) hydrolyze internal 1,4 glycosidic bonds of the polysaccharide chain, thereby yielding new chain ends at the surface of cellulose crystals.

EC 3.2.1.6 enzymes (β-1,3-endoglucanases) hydrolyze internal 1,3 glycosidic bonds of the polysaccharide chain, which also results in the formation of new chain ends at the surface of cellulose crystals.

EC 3.2.1.21 enzymes (β-glucosidases) hydrolyze cellobiose into glucose, a readily fermentable substrate.

EC 3.2.1.91 enzymes (β-1,4-exocellulases) cleave cellobiosyl residues (cellobiose is a glucose dimer) from the chain ends of cellulose.

Particularly preferred enzymes (and hence particularly preferred genes) for use in the present invention are cellulase E2 and cellulase E3 of *T. fusca* and CBH I of *T. reesei*.
Expression Constructs:

Once the protein coding sequence (i.e., the cellulase gene) has been identified and isolated, it must be inserted into an appropriate expression construct containing regulatory elements to direct the expression of the gene and to direct secretion of the gene product or targeting of the gene product to a particular sub-cellular location or organelle. Manipulation of oligonucleotide sequences using restriction endonucleases to cleave DNA molecules into fragments and DNA ligase enzymes to unite compatible fragments into a single DNA molecule with subsequent incorporation into a suitable plasmid, cosmid, or other transformation vector are well-known to the art.

A transcription regulatory sequence must be included in the expression construct in order to direct the transformed plant cells to transcribe the inserted cellulase coding sequence. Transcriptional regulators may be inducible or constituitive. Inducible transcription regulators direct transcription of the downstream coding sequences in a tissue-specific or growth-stage specific manner. Constituitive regulators provide for sustained transcription in all cell tissues. For purposes of the present invention, constructs which provide constituitive expression of the coding sequence are preferred.

It is also preferred that the expression construct contain a transcription initiation sequence from the tumor-inducing plasmid (Ti) of Agrobacterium. Several T-DNA transcription initiation sequences are well known and include, without limitation, the octopine synthase, nopaline synthase, and mannopine synthase initiators.

Downstream of the initiation sequence and fused to the coding sequence, the expression construct may be manipulated to contain a leader signal sequence which directs the resulting polypeptide to a particular organelle or targets the expressed product for secretion (or to signal post-transcriptional or post-translational modification of the gene product).

Likewise, the expression construct should also include a termination sequence to signal transcription termination.

To facilitate selection of successfully transformed plants, the expression construct should also include one or more selectable markers. The neomycin phosphotransferase gene (NPT II), a well-characterized and widely employed antibiotic resistance selection marker is preferred. This marker provides resistance to kanamycin. A large number of other markers are known and can be used with equal success (e.g., other antibiotic resistance markers, dihydrofolate reductase, luciferase, β-glucuronidase, and the like).

Figure 1:
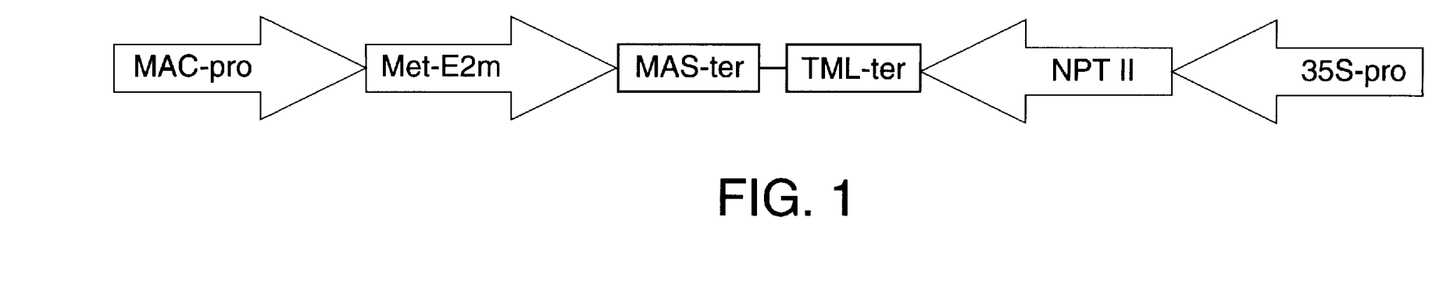
FIG. 1 is a schematic diagram of binary vector T-DNA for an expression construct to transform plants to contain cellulase E2 of *T. fusca*. Promoters and structural genes are depicted as arrows which indicate the direction of transcription. Terminators are depicted as boxes. NPT II=neomycin phosphotransferase; Met-E2m=*T. fusca* E2 (mature form with N-terminal methionine added); MAS-ter=mannopine synthetase terminator; TML-ter=tumor morphology left terminator; MAC-pro=hybrid "MAC" promoter.
Figure 2:
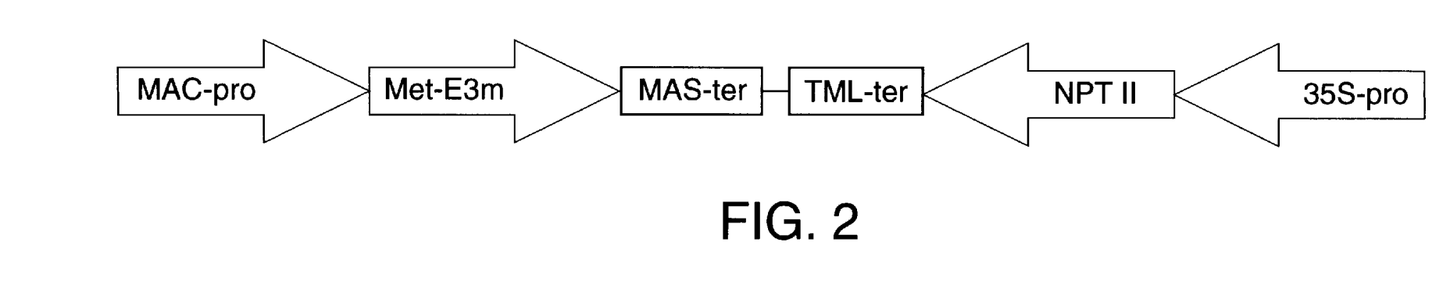
FIG. 2 is a schematic diagram of binary vector T-DNA for an expression construct to transform plants to contain cellulase E3 of *T. fusca*. Promoters and structural genes are depicted as arrows which indicate the direction of transcription. Terminators are depicted as boxes. NPT II=neomycin phosphotransferase; Met-E3m=*T. fusca* E3 (mature form with N-terminal methionine added); MAS-ter=mannopine synthetase terminator; TML-ter=tumor morphology left terminator; MAC-pro=hybrid "MAC" promoter.

FIGS. 1 and 2 depict schematic representations of suitable expression constructs for transformation of plants. These constructs are intended for use with Agrobacterium-mediated transformation using the binary vector approach. However, these same constructs can be coated onto microprojectiles for transformation by particle bombardment. With the exception of the coding sequence, these two constructs are essentially identical: FIG. 1 is a schematic diagram of binary vector T-DNA for an expression construct to transform plants to contain cellulase E2 of *T. fusca*. FIG. 2 is a schematic diagram of binary vector T-DNA for an expression construct to transform plants to contain cellulase E3 of *T. fusca*.

In both FIG. 1 and FIG. 2, promoters and structural genes are depicted as arrows which indicate the direction of transcription and terminators are depicted as boxes. See the "Brief Description of the Figures" for a legend to the abbreviations. In the expression constructs depicted in FIGS. 1 and 2, the "MAC" hybrid promoter drives the transcription of the recombinant cellulase genes. Both constructs also contain a constitutive NPT II expression cassette to allow for antibiotic resistance selection using kanamycin. The coding sequence of the construct shown in FIG. 1 (Met-E2m) encodes cellulase E2 from *T. fusca*. (See SEQ. ID. NO: 1; ATG start codon at nt's 255–257, TGA stop codon at nt's 1578–80, first codon of mature E2 protein (AAT) at nt's 348–350.) This sequence encodes the mature form of the enzyme with an N-terminal methionine added. In the same fashion, the coding sequence of the construct shown in FIG. 2 (Met-E3m) encodes cellulase E3 from *T. fusca*. (See SEQ. ID. NO: 2; ATG start codon at nt's 575–577, TAA stop codon at nt's 2363–65, first codon of mature E3 protein (GCC) at nt's 689–692.) This sequence also encodes the mature form of the enzyme with an N-terminal methionine added. (See the Examples, below.)

Transformation of Plants:

Transformation of the plants can be accomplished by any means known to the art, including Agrobacterium-mediated transformation, particle bombardment, electroporation, and virus-mediated transformation. The method of transformation is not critical to the functionality of the present invention insofar as the method chosen successfully incorporates the oligonucleotide construct containing the cellulase-encoding region and any accompanying regulatory sequences into the plant host. The nature of the plant host to be transformed has some bearing on the preferred transformation protocol. For dicots, Agrobacterium-mediated transformation utilizing protoplasts or leaf disks is most preferred. Although the Examples disclose the use of tobacco and alfalfa as bioreactors for cellulase production, any crop plant, including monocots, can be utilized. Transformation of monocots is typically achieved by particle bombardment of embryogenic cell lines or cultured embryos. See, for instance, Vasil et al. (1993) and Castillo et al. (1994). Recent developments in "super-binary" vectors, however, also allow for the use of Agrobacterium-mediated gene transfer in most of the major cereal crops. See, for instance, Ishida et al. (1996). In this case, the explant source is typically immature embryos.

Agrobacterium-mediated transformation of the plant host using explants is preferred for its relative ease, efficiency, and speed as compared to other methods of plant transformation. For example, disks are punched from the leaves of the plant host and cultured in a suitable medium where they are then exposed to Agrobacterium containing the expression construct and (preferably) a disarmed tumor-inducing (Ti) plasmid. *Agrobacterium tumefaciens* LBA 4404 is the preferred strain for transformation. The preferred binary vector is the pCGN1578 binary vector (McBride and Summerfelt (1990)).

The binary vector transformation method is well known and needs only be briefly described herein. See Zambryski et al. (1989) for a complete review. The Ti plasmid of Agrobacterium contains virulence genes (vir) which encode trans-acting proteins that enable the transfer of a portion of the plasmid (the T-DNA) to a plant cell. The T-DNA portion of the Ti plasmid is flanked by two border regions (the right and left borders) which act as recognition sites for the excision of the T-DNA from the plasmid prior to its transfer to the plant host. Excision of the T-DNA is mediated by the vir genes of the Ti plasmid and involves nicking of the right and left borders of the T-DNA, which frees a single-stranded oligonucleotide fragment. This fragment is then mobilized out of the Agrobacterium and into the plant host target.

In the binary vector method, the T-DNA with its right and left border regions is cloned into *E. coli* in known fashion, and the wild-type genes normally found between the two border regions is excised. The expression construct encoding the cellulase of interest is inserted between the right and left border regions. This construct is designated the "binary plasmid." Construction of the binary plasmid is accomplished utilizing the well-characterized recombinant genetic methods applicable to *E. coli*. Successful transformants are selected utilizing a co-transformed marker appropriate for *E. coli*.

The binary plasmid is then mobilized back into Agrobacterium. This is accomplished by direct transformation procedures well known to those skilled in the art.

The Agrobacterium itself, such as the preferred LBA 4404 strain, is genetically manipulated to contain a Ti plasmid (called the helper plasmid) which lacks the T-DNA and the tumor-inducing regions (i.e., the Ti plasmid is "disarmed") but which still encodes the virulence proteins necessary for DNA transfer. By cooperation between the helper plasmid and the binary plasmid, the length of DNA between the two border regions of the binary plasmid is excised and mobilized into the plant host, where it is incorporated into the plant host genome. The binary method derives its name from the fact that the plasmid containing the expression construct to be transferred is maintained within Agrobacterium as a distinct and independently replicating vector from the Ti plasmid itself.

Selection of successful transformants is accomplished using the co-transformed selection marker discussed above. If the marker is NPT II, selection is accomplished by treatment with kanamycin.

For the present invention, the most preferred plants for transformation are alfalfa and tobacco. However, any plant species will function with comparable success. Included among the plant species which can be utilized in the present invention are cauliflowers, artichokes, apples, bananas, cherries, cucumbers, grapes, lemons, melons, nuts, oranges, peaches, pears, plums, strawberries, tomatoes, cabbages, endive, leeks, lettuce, spinach, arrowroot, beets, carrots, cassava, turnips, radishes, yams, sweet potatoes, beans, peas, soya, wheat, barley, corn, rice, rapeseed, millet, sunflower, oats, tubers, kohlrabi, potatoes, and the like.

The plants to be transformed are preferably common green field plants, such as the preferred alfalfa and tobacco, as well as soya, corn, and the like. Equally preferred are plant hosts which are grown specifically for "biomass energy," such as switchgrass, poplar, and the like. In this instance, the enzymes would not be recovered from the plants. The plants are then transformed and regenerated into whole plants which express fully-functional, cellulose-degrading enzymes in economically significant quantities.

Alfalfa is one of the most preferred plant species for use in the present invention because alfalfa is a hardy, perennial plant, which grows well with minimal fertilization and irrigation. Alfalfa is also a very prolific plant. In temperate areas such as those found in the Midwestern United States, alfalfa will yield three or more harvests per growing season. Methods have also been developed for wet fractionation of the herbage matter to recover value-added products therefrom.

Tobacco is equally preferred for its prolific growth, ease of transformation, and its well-characterized genetics. Both alfalfa and tobacco are widely cultivated throughout the United States and in other parts of the world.

In the most preferred embodiment, alfalfa or tobacco plants are stably transformed to express, constituitively, enzymatically active E2 or E3 cellulases from *T. fusca*. Also preferred are alfalfa or tobacco which express enzymatically active CBH I from *T. reesei* or combinations of E2, E3, and CBH I. The *T. fusca* cellulases are most preferred because they are native to thermo-tolerant bacteria and are relatively heat stable. This allows isolation of the cellulase from plant material using relatively rigorous heat precipitation without adversely effecting the activity of the cellulase.

Stage-Specific and Tissue-Specific Expression of Cellulases:

Because the enzymes to be expressed by the transformed plant hosts hydrolyze components of the plant cell wall, high levels of expression might have a deleterious effect on the plant host. Therefore, targeting of the expressed enzyme to particular sub-cellular compartments may be preferred. Targeting of the expressed enzyme may also be preferred to avoid expression of the enzyme in sub-cellular compartments where proteolytic activity is high. Targeting of the expressed enzyme may also be preferred if the exogenous cellulase activity interferes with the normal cellular metabolism of certain compartments.

For instance, targeting expression to the apoplast allows the exogenous protein to avoid the more active protein-degrading systems of other cellular compartments, such as in plant leaf vacuoles.

Several signal sequences are known and can be utilized in the present invention. For example, signal sequences for targeting to the secretory pathway are known, Wandelt et al. (1992), Bednarek (1991), Mason et al. (1988), as are sequences for targeting to the chloroplast, Keegstra et al. (1993), and the mitochondrion, de Castro Silva Filho et al. (1996).

For apoplast targeting, the VSP leader is preferred. The VSP leader comprises the amino acid sequence: $NH_3$-Met-Lys-Leu-Phe-Val-Phe-Phe-Val-Ala-Ala-Val-Val-Leu-Val-Ala-Trp-Pro-Cys-His-Gly-Ala- (SEQ. ID. NO: 3). See Mason et al. (1988).

Additionally, bacterial secretory sequences found in the wild-type cellulase gene may be removed to afford cytoplasmic expression of the enzyme in the recombinant plant host.

Targeting can be achieved by fusing combinations of mitochondrial and chloroplast targeting signals to the N-terminus of the desired cellulase, as has been demonstrated for the reporter genes chloramphenicol acetyl transferase and β-glucuronidase, de Castro Silva Filho et al. (1996). In some cases, efficient translocation requires the presence of both signal peptides, with the amino terminal peptide being crucial in specifying import into a particular organelle. In addition, vacuole targeting can be achieved by fusing the sequence encoding the N-terminal 146 amino acids of the vacuolar patatin protein between a secretory leader and structural gene for the cellulase, as has been demonstrated for the yeast invertase gene, Sonnewald et. al. (1991).

Regeneration of Mature Transgenic Plants:

Transgenic tobacco and alfalfa were produced by Agrobacterium-mediated transformation using explants as source material. This is a routine method easily followed by those skilled in the art. The production methods for transgenic tobacco and alfalfa are given as non-limiting illustrations of the practice of the invention.

The transformation procedure for tobacco is essentially the explant method developed by Horsh et al. (1985). Leaf explants are taken from the second and third fully expanded leaves of three-week old in vitro shoot cultures of *Nicotiana tabacum* W38 maintained on MS medium, Murashige and Skoog (1962). The leaf pieces are cut into 1 cm squares and pre-cultured on MS medium with 2.0 mg/L 6-benzyl-aminopurine (BAP) and 0.1 mg/L alpha-naphthalene acetic acid (NAA) for 24 hours at 25° C. with a 16 hour photo period of 70–90 $\mu E$ $m^{-2}s^{-1}$. After pre-culture, explants are placed into a suspension of Agrobacterium cells. After 30 minutes, leaf explants are blotted on filter paper and placed abaxial-side down on MS medium with 1.0 mg/L BAP and 0.1 mg/L NAA and co-cultivated for four days under the same conditions as given above. Leaf pieces are then rinsed three times in sterile water, blotted on filter paper, and transferred to the media used for co-cultivation but containing 100 mg/L kanamycin and 400 mg/L carbenicillin. Plantlets (typically 2–3) develop 10–14 days later from callus formed along cut leaf edges. If desired, further plantlet formation can be achieved by transfer of explants to fresh medium at two week intervals. Plantlets are excised and rooted on MS media containing 100 mg/L kanamycin and 400 mg/L carbenicillin.

To transform alfalfa, new-growth trifoliates are taken from alfalfa plants (regenerable genotypes, Bingham et al. (1975)) maintained in a growth room and sterilized using alcohol and bleach washes (30 seconds in 70% alcohol, 90 seconds in 20% hypochlorite+0.1% SDS, followed by three rinses in sterile distilled water). Leaf edges are cut on moist filter paper and tissue then placed into liquid SH-II medium. (Bingham et al., supra.) When sufficient explants have been taken, the explants are moved to a suspension of Agrobacterium cells containing the engineered plasmid. (The Agrobacterium suspension is taken from an overnight culture grown in liquid YEP selection medium.) Cell density is adjusted to fall between about 0.6 to about 0.8 at $A_{660}$. After 30 minutes inoculation, the explants are gently blotted on filter paper and placed on B5H medium, Brown and Atanassov (1985), for four days. They are then rinsed twice in sterile water and cultured on B5H for a further four days. At the end of this period, they are rinsed three times and transferred to B5H containing 25 mg/L kanamycin and 250 mg/L carbenicillin. Plates are maintained at 24° C., 16 hour photo period, light intensity 60–80 $\mu E$ $m^{-2}s^{-1}$. Explant-derived calli (and occasionally embryoids) which form within 3 weeks on this medium are moved to B5H with antibiotics but without hormones to allow for further embryoid production and development of existing embryoids. After three to four weeks, embryos are transferred to MS medium including the two antibiotics to allow for development into plantlets. Callus forms on untreated explants in the presence of 25 mg/L kanamycin but embryos are never produced. Each explant piece can give rise to multiple (up to 40) embryos. Plantlets are rooted on MS medium lacking antibiotics.

Monitoring Cellulase Expression:

Cellulase expression can be monitored using a number of different methods, the two most common being western blot analysis (which detects cellulase protein using antibodies specific for the cellulase of interest) and zymographic analysis or enzyme assay (both of which measure the ability of the expressed cellulase to degrade a cellulosic substrate).

Briefly, in the western blot technique, whole plant samples (or root tips, leaves, etc.) are ground in an extraction buffer (preferably 50 mM sodium acetate (pH 5.5) and 10 mM dithiothreitol) and an aliquot of the extract loaded onto an electrophoresis gel (e.g., polyacrylamide containing SDS). Preferably, identical extractions are performed on non-transformed plants and aliquots of these extractions are then loaded onto parallel lanes of the gel to act as negative controls. Serial dilutions of purified cellulase standards can be also electrophoresed to act as positive controls. The gel is then subjected to electrophoresis in standard and well known fashion.

After electrophoresis is complete, the separated proteins are electro-transferred to a nitrocellulose, PVDF, or nylon membrane, in well known fashion. The membrane containing the immobilized proteins is then immersed in a non-specific blocking buffer or detergent (e.g., "TWEEN 20"), and then placed in a solution containing an antibody (the primary antibody) which is specifically reactive with the particular cellulase under investigation. The membrane is then washed and exposed to an enzyme-antibody conjugate directed against the primary antibody (e.g., goat anti-rabbit IgG). The membrane is then exposed to a chromogenic or luminescent substrate to visualize cellulase hybridization on the membrane.

Zymograms in which the cellulase of interest is resolved in a gel system and then assayed for activity within the gel provide a relatively simple way to assess the activity of cellulases in crude cell lysates. See Coughlan (1988). In this approach, plant tissue is ground in the presence of an appropriate grinding buffer (100 mM Tris-HCl pH 9.0, 5 mM 2-mercaptoethanol, 1 mM phenylmethanesulfonyl fluoride, 0.5 mM ethylenediamine-tetraacetic acid, for example). After grinding of the tissue, an equal volume of a 50% (v/v) slurry of washed polyvinylpolypyrrolidone (suspended in grinding buffer) is added and mixed thoroughly. After centrifugation of the mixture, a sample of the cleared extract is subjected to electrophoresis through a non-denaturing (8%, w/v) polyacrylamide gel. The resulting gel is used to prepare a sandwich with a thin film (<2 mm) of agarose (0.7% agarose, 0.5% Sigma medium viscosity carboxymethycellulose) bonded to "GELBOND" film (FMC Corporation). After incubation for 1.5 hours at 50° C., the agarose film is stained with "CONGO RED" dye for 30 minutes followed by a 1M NaCl wash. After several minutes, it is possible to visualize cellulase activity as a clear zone within a background of red staining.

Cellulase activity is most commonly assayed in aqueous solution, using a cellulosic substrate and monitoring the reaction for either the release of a chromophore/fluorophore or release of cellobiose ("reducing sugar"). For example, *T. fusca* E2 activity can be measured by incubating a sample of the enzyme in a 0.4 ml reaction containing 1% (w/v) low viscosity carboxymethylcellulose (Sigma C-5678) and 50 mM NaOAc pH 5.5 at 55° C. for 2–20 hours. 1.0 ml of DNS solution, see Irwin et al. (1993), is then added and the mixture is boiled for 15 minutes. Measurement of absorbance values at 600 nm for each reaction can then be correlated to values determined for a known series of glucose standards to determine the extent of carboxymethylcellulose hydrolysis. For plant extracts, background values are determined by preparing parallel reaction samples which contain no substrate and subtracting this value from that obtained in the presence of 1% carboxymethylcellulose.

For a more complete discussion of cellulase assays, see Adney et al. (1994), Baker et al. (1992), Tucker et al. (1989) and Irwin et al. (1993).

Isolation of Cellulase Activity from Plants:

It is most preferred that, where applicable, the enzyme not be purified from the plant material, but rather that the plant material containing the cellulase activity be used directly. This is demonstrated in the Examples, below, where transgenic alfalfa which expressed cellulase activity is added directly to silage materials to further the extent of fermentation.

If isolation of the cellulase activity is desired, this can be accomplished by any means known to the art. For example, the preferred *T. fusca* E2, E3, and CBH I enzymes are taken from thermo-tolerant bacteria. The activity of these enzymes remains unchanged by treatments up to about 55–60° C. Therefore, these enzymes can be isolated by gently heating the plant material in aqueous buffered solution (100 mM Tris/HCl pH 9.0, for example) to precipitate the bulk of plant proteins. The soluble cellulase enzymes are then recovered and further purified by any means known to the art, including HPLC, affinity chromatography, and the like. To facilitate downstream processing of the enzyme, a purification tag may optionally be incorporated into the expressed cellulase.

Since the above-mentioned enzymes are well-characterized, the preferred purification scheme is based on established protocols already in existence. For example, *T. fusca* E2 from a heat-treated plant extract is further purified by adsorption to a phenyl "SEPHAROSE" column in the presence if 0.8 M ammonium sulfate. Successive column washes using ammonium sulfate concentrations of 0.6 M and 0.3 M in a buffer containing 5 mM KPi, pH 6.0 and 5 mM NaCl are followed by a final wash with 0.1 M KPi, pH 6.0. Elution of E2 is accomplished using 5 mM KPi, pH 6.0. Peak fractions are loaded on a hydroxylapatite column (equilibrated with 1 mM KPi, pH 6.0) and the flow-through fractions collected and pooled. The pooled fractions are loaded on a "Q-SEPHAROSE" column (pre-equilibrated with 10 mM BisTris, pH 6.0) and eluted with a continuous buffer gradient from 5 mM BisTris, pH 6.0 to 150 mM NaCl, 5 mM BisTris, pH 6.0. Peak fractions from the "Q-SEPHAROSE" column are then pooled, concentrated and stored frozen in convenient aliquots. Similarly detailed protocols exist for both *T. fusca* E3 and *T. reesei* CBH I, see Irwin et al. (1993).

EXAMPLES

The following Examples are included solely to aid in a more complete understanding of the manufacture and use of the transgenic plants disclosed and claimed herein. The Examples do not limit the scope of the invention in any fashion.

Example 1

Production of Transgenic Alfalfa and Tobacco Which Express Cellulase "E2" of *T. fusca*

Transgenic alfalfa and tobacco plants were produced using the same protocol. Binary vectors carrying recombinant cellulase expression cassettes were transformed into *Agrobacterium tumefaciens* strain LBA 4404, facilitating Agrobacterium-mediated transformation of plant tissue. The construct used is shown in FIG. 1. The gene encoding the E2 cellulase of *Thermomonospora fusca* was obtained as described by Ghangas & Wilson (1988). The E2 gene was modified by PCR using the XbaE2 primer, 5'-GCTCTAG *ATG*AATGATTCTCCGTTC-3' (SEQ. ID. NO: 4) and the "–20 sequencing primer," 5'-TGACCGGCAGCAAAATG-3' (SEQ. ID. NO: 5), (product #1211, New England Biolabs, Inc., Beverly, Mass.), resulting in a recombinant gene in which an Xba I site (bold italics) was incorporated immediately 5' to an introduced start codon (underlined). This start codon precedes the first codon encoding the mature form of the E2 protein (AAT, nt's 348–350 in SEQ. ID. NO: 1). The net effect of these changes is the removal of the bacterial secretion signal peptide (resulting in cytosolic accumulation), the addition of a novel cloning site to facilitate expression cassette construction and the addition of a methionine residue to the N-terminus of the protein compared to the processed mature form of E2 obtained from *T. fusca*).

The cloned E2 gene required no modification at the 3' end as a convenient Eco RI restriction site occurs approximately 45 nucleotides 3' to the stop codon.

The preferred expression cassette includes the hybrid "MAC" promoter and the mannopine synthetase terminator. The MAC promoter contains distal elements, including the transcriptional enhancer, of the CaMV 35S promoter (−940 to −90, relative to the mRNA start site), as well as proximal promoter elements derived from the Agrobacterium mannopine synthetase promoter (−301 to +65 relative to the mRNA start site). MAC has been reported to result in higher levels of expression than either of the natural promoters (Comai et al. (1990).) The expression cassette was cloned into the pCGN1578 binary vector and mobilized into Agrobacterium.

Figure 3:
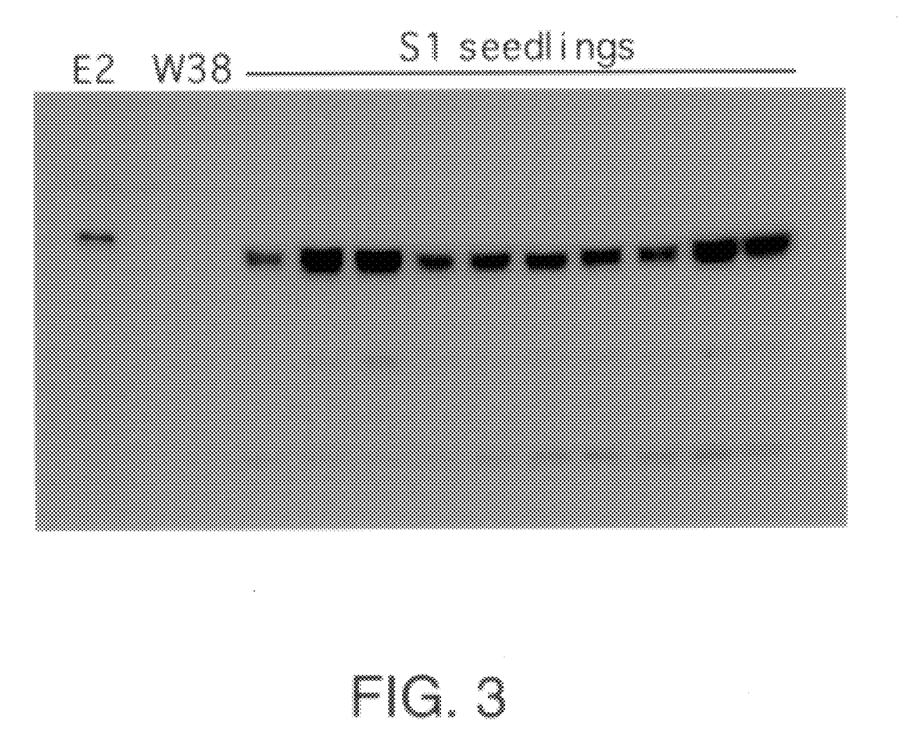
FIG. 3 is a western blot analysis evidencing the expression of *T. fusca* E2 cellulase in tobacco transformed to contain the expression construct depicted in FIG. 1.

Initial tobacco transformants were screened by western blot to determine the level of expression. Levels of expression ranged up to 0.1 to 0.2% of extracted protein. The mature plants were allowed to self and set seed. One of the initial transformants, designated CT30, was tested further to verify the sexual transmission of the transgene. S1 seeds from this plant were germinated and tested for kanamycin resistance. Leaf samples from $kan^R$ seedlings as well as a W38 control were prepared for western blot analysis as described previously. The results are depicted in FIG. 3. Each lane contained extract corresponding to 5 mg fresh weight of leaf tissue. In addition, 1 ng of purified E2 enzyme was loaded as a control. Levels of expression were similar to that observed in the parental transformant, demonstrating the stable sexual transfer of this trait. Similar genetic stability was also observed in alfalfa plants transformed with this transgene.

Figure 5:
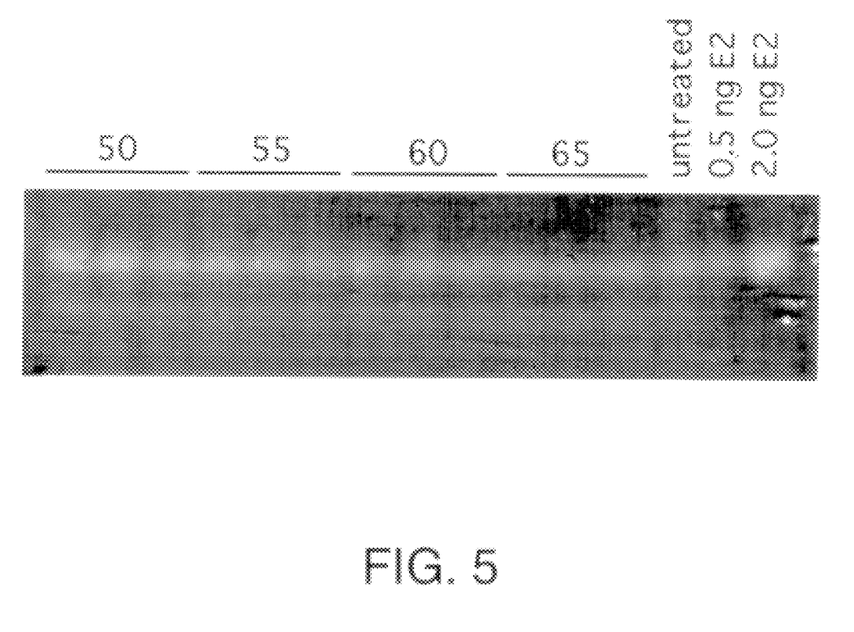
FIG. 5 is a zymogram gel assay evidencing the expression of active *T. fusca* E2 cellulase in alfalfa transformed to contain the expression construct depicted in FIG. 1.

The thermal stability and enzymatic activity of recombinant T. fusca E2 was demonstrated using transgenic alfalfa. Samples were prepared for zymogram analysis as described above. As shown in FIG. 5, aliquots of alfalfa extract were treated for 5, 10 and 20 minutes (grouped from left to right) at each of the temperatures indicated (°C.) before being subjected to native gel electrophoresis. An untreated sample of extract and two purified E2 standards were included as controls. Levels of E2 activity corresponded well with expected activity based on western blot analysis of samples from the same plant. In addition, no significant loss in band intensity (activity) was observed at any of the treatment temperatures, despite the fact that greater than 95% of the soluble protein in the extract is denatured after 20 minutes at 65° C.

Example 2

Production of Transgenic Alfalfa and Tobacco Which Express Cellulase "E3" of T. fusca Here, the expression construct depicted in FIG. 2 was used to transform alfalfa and tobacco using the same methodology as described in Example 1.

The gene encoding the E3 cellulase of Thermomonospore fusca was obtained as described by Zhang et al. (1995). The 5' end of the E3 gene was modified by PCR using the primer XbaE3, 5'-GCTCTAG<u>AT</u>GGCCGGCTGCTCGGTG-3' (SEQ. ID. NO: 6), resulting in a recombinant gene in which an Xba I site (bold italics) was incorporated immediately 5' to an introduced start codon (underlined). This start codon precedes the first codon encoding the mature form of the E3 protein (GCC, nt 689–691 in SEQ. ID. NO: 2). The 3' end of the E3 gene was modified using the primer RIE3, 5'-GGAATTC<u>TTA</u>CAGAGGCGGGTAG-3' (SEQ. ID. NO: 7), thereby placing an Eco RI restriction site (bold italics) immediately 3' to the stop codon (underlined) for the E3 gene. Note that this latter primer is homologous to the noncoding strand of the E3 gene. The net effect of these changes is the removal of the bacterial secretion signal peptide (resulting in cytosolic accumulation), the addition of novel cloning sites to facilitate expression cassette construction and the addition of a methionine residue to the N-terminus of the protein (compared to the processed, mature form of E3 obtained from T. fusca).

The E3 expression cassette was constructed as described above for the E2 cassette.

Figure 4:
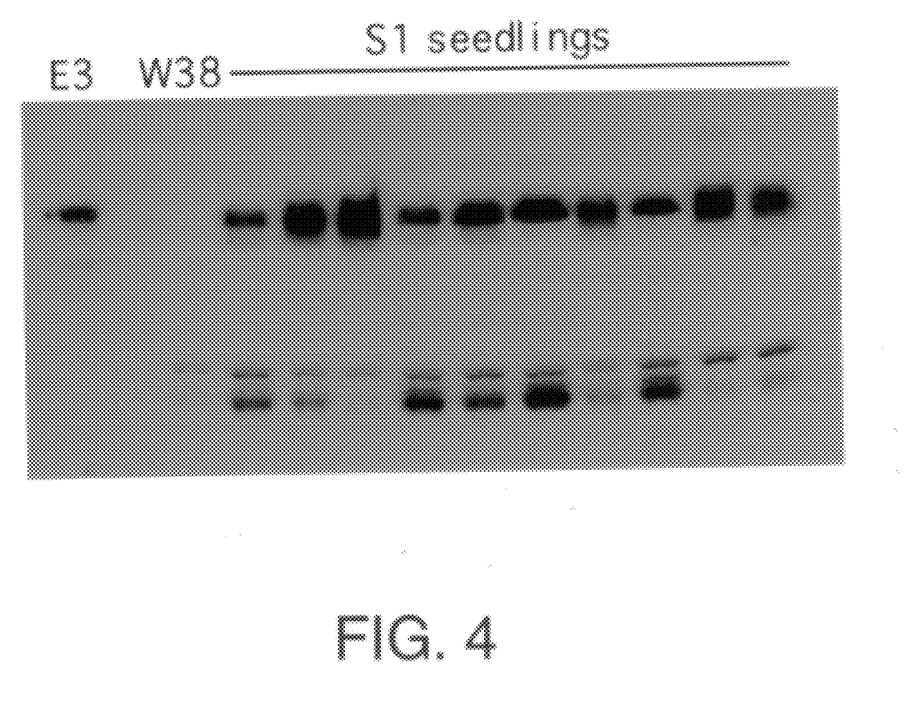
FIG. 4 is a western blot analysis evidencing the expression of *T. fusca* E3 cellulase in tobacco transformed to contain the expression construct depicted in FIG. 2.

Initial tobacco transformants were screened by western blot to determine the level of expression. Levels of expression ranged up to about 0.04% of extracted protein. The mature plants were allowed to self and set seed. One of the initial transformants, designated CT117, was tested further to verify the sexual transmission of the transgene. S1 seeds from this plant were germinated and tested for kanamycin resistance. Leaf samples from $kan^R$ seedlings as well as a W38 control were prepared for western blot analysis as described previously. The results are depicted in FIG. 4. Each lane contained extract corresponding to 5 mg fresh weight of leaf tissue. In addition, 1 ng of purified E3 enzyme was loaded as a control. Levels of expression were comparable to that observed in the parental transformant, demonstrating the stable sexual transfer of this trait.

Example 3

Sexual Transfer of Cellulase Expression in Tobacco and Alfalfa

Original transgenic lines of tobacco and alfalfa shown to express either E2 or E3 cellulase were used in sexual crosses. In both cases, the trait segregated in progeny as predicted by Mendelian genetics. Expression levels were the same as, or greater than those seen in parental lines.

Example 4

Use of Transgenic Alfalfa in Silage

Here, regular non-transformed alfalfa, alfalfa transformed according to Example 1 and alfalfa transformed according to Example 2 were ensiled under identical conditions for one month and the products of fermentation for each experiment quantified. The results are presented in Table 2.

All of the ensiled plant material was ground separately through a manual meat grinder. The grinder was rinsed with water and wiped with ethanol after grinding each sample. A 1 to 1 to 1 mixture of non-transformed alfalfa, E2-transformed alfalfa, and E3-transformed alfalfa was ground together and used to assemble two control silos (Cont1 and Cont2, 50 g each). The two control silos were inoculated with a 1 mL of a commercial inoculant (0.1098 g "BIOMATE LP/PC" concentrate in 500 mL sterile water).

Two silos each of E2-transformed alfalfa (E2-1, E2-2) and E3-transformed alfalfa (E3-1, E3-2) were constructed in the same fashion as the controls (35 g each, inoculated with 0.6 mL of the above-noted inoculant). Two silos of mixed E2- and E3-transformed alfalfa were constructed by grinding together 17.5 g each of E2- and E3-transformed alfalfa per silo (35 g each, inoculated with 0.6 mL of the above-noted inoculant).

All of the silos were then placed into a 30° C. water bath until opening.

Of special note in this Example is the increased amount of fermentation products in the transgenic alfalfa as compared to the non-transformed alfalfa. In particular, note that a mixture of alfalfa herbage expressing both the E2 and E3 cellulases exhibits markedly improved fermentation yield as compared to the non-transformed alfalfa and ensiled alfalfa expressing either E2 or E3 enzymes.

Clearly, as shown by this Example, expression of cellulases in transgenic alfalfa leads to better silage production.

The invention is not limited to the preferred embodiments, transformation protocols, transformed plant hosts, and expression constructs explicitly described above, but encompasses all such forms thereof as are encompassed within the scope of the attached claims.

Castillo et al. (1994), Rapid production of fertile transgenic plants of Rye. Bio/Technology 12:1366–1371.

Comai et al. (1990), Novel and useful properties of a chimeric plant promoter combining CaMV 35S and MAS elements. Plant Mol. Biol. 15:373–381.

Coughlan, M. P. (1988), Staining Techniques for the Detection of the Individual Components of Cellulolytic Enzyme Systems. Methods in Enzymology 160:135–144.

Current Protocols in Molecular Biology, Volumes 1–3, Series Editor, Virginia Benson Chanda, ©1987–1997, John Wiley & Sons, Inc.

TABLE 2

Organic Acid Analysis (OAA) via HPLC

| Sample ID | % DM | pH | SUC | LAC | FOR | ACE | PRO | 2,3 But | ETOH | BUT | Total Prod. | Avg. Total Prod. |
|---|---|---|---|---|---|---|---|---|---|---|---|---|
| Cont 1 | 23.33612 | 5.741 | 0.144 | 2.014 | 0.000 | 1.764 | 0.000 | 0.239 | 0.704 | 0.000 | 4.86 | 5.47 |
| Cont 2 | 21.62983 | 5.121 | 0.159 | 3.885 | 0.000 | 1.407 | 0.328 | 0.000 | 0.294 | 0.000 | 6.07 | |
| E2-1 | 22.99369 | 5.277 | 0.157 | 3.390 | 0.000 | 2.300 | 0.233 | 0.000 | 0.330 | 0.000 | 6.41 | 6.09 |
| E2-2 | 23.83774 | 5.166 | 0.361 | 2.935 | 0.000 | 1.998 | 0.177 | 0.000 | 0.298 | 0.000 | 5.77 | |
| E3-1 | 22.88773 | 5.128 | 0.283 | 3.321 | 0.000 | 2.380 | 0.177 | 0.000 | 0.292 | 0.000 | 6.45 | 6.61 |
| E3-2 | 22.22822 | 5.151 | 0.354 | 3.324 | 0.000 | 2.608 | 0.200 | 0.000 | 0.288 | 0.000 | 6.77 | |
| E23-1 | 22.95945 | 5.743 | 0.551 | 2.848 | 0.000 | 3.185 | 0.328 | 0.000 | 0.337 | 0.000 | 7.25 | 7.45 |
| E23-2 | 22.66411 | 5.888 | 0.602 | 2.745 | 0.000 | 3.649 | 0.301 | 0.000 | 0.353 | 0.000 | 7.65 | |

The table headings are as follows:
% DM = percent dry matter of silage,
pH = acidity,
SUC = succinic acid,
LAC = lactic acid,
FOR = formic acid,
ACE = acetic acid,
PRO = propionic acid,
2,3 But = 2,3-butanediol,
ETOH = ethanol,
BUT = butyric acid,
Cont 1 and Cont 2 = controls,
E2-1 and E2-2 = transformant expressing E2,
E3-1 and E3-2 = transformants expressing E3,
E23-1 and E23-2 = a 1:1 mixture of herbage from transgenic alfalfa expressing E2 and E3.

BIBLIOGRAPHY

Adney et al. (1994), Cellulase assays. In: Enzymatic conversion of biomass for fuels production, Eds. M. E. Himmel, J. O. Baker & R. P. Overend. ACS symposium series 566.

Aspegren et al. (1995), Secretion of a heat-stable fungal β-glucanase from transgenic, suspension-cultured barley cells. Molecular Breeding 1:91–99.

Baker et al. (1992), Thermal denaturation of T. reesei cellulases studied by differential scanning calorimetry and tryptophan fluorescence. Apply. Biochem. Biophys. 34:217–231.

Bednarek (1991), The barley lectin carboxy-terminal peptide is a vacuolar protein sorting determinant in plants. The Plant Cell 3:1195–1206.

Belkacemi et al. (1996), Enzymatic hydrolysis of timothy grass pretreated by ammonia fiber explosion. In: Liquid fuels and industrial products from renewable resources, Proceedings of the third liquid fuel conference, Eds. J. S. Cundiff, E. E. Gavett, C. Hansen, C. Peterson, M. A. Sanderson, H. Shapouri & D. L. VanDyne. ASAE publication 08-96 pp 232–240.

Bingham et al. (1975), Breeding alfalfa which regenerates from callus tissue in culture. Crop Sci. 15:719–721.

Brown and Atanassov (1985), Role of genetic background in somatic embryogenesis in Medicago. Plant Cell Tissue Organ Culture 4:107–114.

Carrer et al. (1993), Kanamycin resistance as a selectable marker for plastid transformation in tobacco. Mol. Gen. Genet. 241:49–56.

de Castro Silva Filho et at. (1996), Mitochondrial and chloroplast targeting sequences in tandem modify protein import specificity in plant organelles. Plant Mol. Biol. 30:769–780.

Divne et al. (1994), The three-dimensional crystal structure of the catalytic core of cellobiohydrolase I from Trichoderma reesei. Science 265:524–528.

Ghangas & Wilson (1988), Cloning of the Thermomonospora fusca endoglucanase E2 gene in Streptomyces lividans: Affinity purification and functional domains of the cloned gene product. Appl. Envir. Microbiol. 54:2521–2526.

Grohmann et al. (1992), Potential for fuels from biomass and wastes. In: Emerging technologies for materials and chemicals from biomass, Eds. R. M. Powell, T. P. Schultz and R. Narayan. ACS symposium series 576.

Henrissat et al. (1995), Synergism of cellulases from Trichoderma reesei in the degradation of cellulose. Bio/Technology 3:722–726.

Horsh et al. (1985), A simple and general method for transferring genes into plants. Science 227:1229–1231.

Irwin et al. (1993), Activity studies of eight purified cellulases: Specificity, synergism, and binding domain effects. Biotechnol. Bioeng. 42:1002–1013.

Ishida et al. (1996), High efficiency transformation of maize mediated by Agrobacterium tumefaciens. Nature Biotechnology 14:745–750.

Keegstra et al. (1993), Targeting of proteins into chloroplasts. Physiologia Plantarum 93:157–162.

Lao et al. (1991), *J. Bacteriol.* 173:3397–3407.

Mason et al. (1988), Proteins homologous to leaf glycoproteins are abundant in stems of dark-grown soy bean seedlings. Analysis of proteins and cDNAs. *Plant Mol. Biol.* 11:845–856.

McBride and Summerfelt (1990), Improved binary vectors for Agrobacterium mediated plant transformation. *Plant Mol. Biol.* 14:269–276.

McBride et al. (1994), Controlled expression of plastid transgenes in plants based on a nuclear DNA-encoded and plastid-targeted T7 RNA polymerase. *Proc. Natl. Acad. Sci. USA* 91:7301–7305.

Micelli et al. (1996), Integrated treatments of steam explosion and enzymatic hydrolysis to produce energetic and industrial products from lignocellulosic biomasses. *Agro-food-Industry Hi-tech* 7:25–28.

Murashige and Skoog (1962), A revised medium for rapid growth and bioassays with tobacco tissue cultures. *Physiol. Plant* 15:473–497.

Pentilla et al. (1987), *Yeast* 3:175–185.

Sonnewald et. al. (1991), Transgenic tobacco plants expressing yeast-derived invertase in either the cytosol, vacuole or apoplast: a powerful tool for studying sucrose metabolism and sink/source interactions. *The Plant J.* 1:95–106.

Spezio et al. (1993), Crystal structure of the catalytic domain of a thermophilic endocellulase. *Biochemistry* 32:9906–9916.

Tucker et al. (1989), Ultra-thermostable cellulases from *Acidothermus cellulolyticus* comparison of temperature optima with previously reported cellulases. *Biotechnology* 7:817–820.

Vasil et al. (1993), Rapid production of transgenic wheat plants by direct particle bombardment of cultured immature embyros. *Bio/Technology* 11:1553–1558.

Wandelt et al. (1992), Vicilin with carboxy-terminal KDEL is retained in the endoplasmic reticulum and accumulates to high levels in the leaves of transgenic plants. *Plant J.* 2:181–192.

Zambryski, P., J. Tempe, and J. Schell (1989), Transfer and function of T-DNA genes from Agrobacterium Ti and Ri plasmids in plants. *Cell* 56:193–201.

Zhang et al. (1995), Characterization of a *Thermomonospora fusca* exocellulase. *Biochemistry* 34:3386–3395.

---

What is claimed is:

1. A genetically recombinant plant comprising a plant transformed to contain and express one or more exogenous gene sequences selected from the group consisting of SEQ. ID. NO: 1, SEQ. ID. NO: 2, and combinations thereof.

2. The genetically recombinant plant of claim 1, wherein the gene product or products are expressed constituitively.

3. The genetically recombinant plant of claim 1, wherein the gene product or products are expressed stage-specifically.

4. The genetically recombinant plant of claim 1, wherein the gene product or products are expressed tissue-specifically.

5. The genetically recombinant plant of claim 4, wherein the gene product or products are expressed in a plant tissue selected from the group consisting of seeds, fruit, stems, leaves, and tubers.

6. The genetically recombinant plant of claim 4, wherein the plant contains two exogenous gene sequences and wherein their respective gene products are expressed independently of one another.

7. The genetically recombinant plant of claim 1, wherein the gene product or products are expressed in a targeted sub-cellular compartment.

8. The genetically recombinant plant of claim 7, wherein the gene product or products are expressed in a sub-cellular compartment selected from the group consisting of: plastid, cytosol, endoplasmic reticulum, mitochondrion, inclusion body, and vacuole.

9. The genetically recombinant plant of claim 7, wherein the plant contains two exogenous genes and wherein their respective gene products are expressed independently of one another.

10. The genetically recombinant plant of claim 1, wherein the gene product or products are expressed extra-cellularly.

11. The genetically recombinant plant of claim 1, wherein the plant is dicotyledonous.

12. The genetically recombinant plant of claim 1, wherein the plant is monocotyledonous.

13. The genetically recombinant plant of claim 1, which is alfalfa or tobacco.

14. A method for producing cellulose-degrading enzymes comprising cultivating a genetically recombinant plant according to claim 1.

15. The method of claim 14, further comprising concentrating the cellulose-degrading enzymes.

16. A method for producing cellulose-degrading enzymes comprising cultivating a genetically recombinant plant according to claim 13.

17. The method of claim 16, further comprising concentrating the cellulose-degrading enzymes.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 1621 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(vi) ORIGINAL SOURCE:
        (A) ORGANISM: Thermomonospora fusca cellulase E2

(xi) SEQUENCE DESCRIPTION: SEQ ID NO:1:

```
CGATATGGAT GATCTGACGT CTGAATCCCC TTGTCACCCT AGACATTCAC CCATTTTGTC      60

GCTTTTACGG CTTTCTTTGG GAGTTCTCCG TTTCACCAAG GAACAAAACC GCAACGGAGA     120

GTAGGCGCGG TCTTTACAGC TCCCTTGCCA ATGGTTATCG TCCGAACGGA AAACGATCTG     180

GGAGCGCTCC CAGCCATGCG CTCCTCTTCG TGCCCCTCAC TTCTTTTGAG CCTTGTGCTC     240

GTTAGGAGCC CCGAATGTCC CCCAGACCTC TTCGCGCTCT TCTGGGCGCC GCGGCGGCGG     300

CCTTGGTCAG CGCGGCTGCT CTGGCCTTCC GGTCGCAAGC GGCGGCCAAT GATTCTCCGT     360

TCTACGTCAA CCCCAACATG TCCTCCGCCG AATGGGTGCG GAACAACCCC AACGACCCGC     420

GTACCCCGGT AATCCGCGAC CGGATCGCCA GCGTGCCGCA GGGCACCTGG TTCGCCCACC     480

ACAACCCCGG GCAGATCACC GGCCAGATCG ACGCGCTCAT GAGCGCCGCC CAGGCCGCCG     540

GCAAGATCCC GATCCTGGTC GTGTACAACG CCCCGGGCCG CGACTGCGGC AACCACAGCA     600

GCGGCGGCGC CCCCAGTCAC AGCGCCTACC GGTCCTGGAT CGACGAATTC GCTGCCGGAC     660

TGAAGAACCG TCCCGCCCAC ATCATCGTCG GGCCGGACCT GATCTCGCTG ATGTCGAGCT     720

GCATCCAGCA CGTCCAGCAG GAAGTCCTGG AGACGATGGC GTACGCGGGC AAGGCCCTCA     780
```

```
AGGCCGGGTC CTCGCAGGCG CGGATCTACT TCGACGCCGG CCACTCCGCG TGGCACTCGC      840

CCGCACAGAT GGCTTCCTGG CTCCAGCAGG CCGACATCTC CAACAGCGCG CACGGTATCG      900

CCACCAACAC CTCCAACTAC CGGTGGACCG CTGACGAGGT CGCCTACGCC AAGGCGGTGC      960

TCTCGGCCAT CGGCAACCCG TCCCTGCGCG CGGTCATCGA CACCAGCCGC AACGGCAACG     1020

GCCCCGCCGG TAACGAGTGG TGCGACCCCA GCGGACGCGC CATCGGCACG CCCAGCACCA     1080

CCAACACCGG CGACCCGATG ATCGACGCCT TCCTGTGGAT CAAGCTGCCG GGTGAGGCCG     1140

ACGGCTGCAT CGCCGGCGCC GGCCAGTTCG TCCCGCAGGC GGCCTACGAG ATGGCGATCG     1200

CCGCGGGCGG CACCAACCCC AACCCGAACC CAACCCGAC GCCCACCCCC ACTCCGACCC      1260

CCACGCCGCC TCCCGGCTCC TCGGGGGCGT GCACGGCGAC GTACGATC GCCAACGAGT       1320

GGAACGACGG CTTCCAGGCG ACCGTGACGG TCACCGCGAA CCAGAACATC ACCGGCTGGA     1380

CCGTGACATG GACCTTCACC GACGGCCAGA CCATCACCAA CGCCTGGAAC GCCGACGTGT     1440

CCACCAGCGG CTCCTCGGTG ACCGCGCGGA ACGTCGGCCA CAACGGAACG CTCTCCCAGG     1500

GAGCCCCCAC AGAGTTCGGC TTCGTCGGCT CTAAGGGCAA CTCCAACTCT GTTCCGACCC     1560

TTACCTGCGC CGCCAGCTGA CCCCTCCTGG CAGTGCACTG GGTGGCTTAG GCGTGCTGGG     1620

G                                                                    1621

(2) INFORMATION FOR SEQ ID NO:2:

(i) SEQUENCE CHARACTERISTICS:
        (A) LENGTH: 3503 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Thermomonospora fusca cellulase E3

(xi) SEQUENCE DESCRIPTION: SEQ ID NO:2:

CGGCGATCCC CCTCATCATT CAGGTGCGGT TAGTTCCCCC AGGCTACCGA GGACCGAATT       60

TCGGTCCGTT TTTCTTGCGG CGAGCCCTGA GACCGTTTCC TGTTCCGTTC CGTCACCATC      120

CTTGCGCGTC CCGGCGGAGG GGGGAAGCAC CCCGCGAGAT GGCTCCGCCA CGGCCTGTTT      180

CCGACCCCCG TCACAAAAGC CCATTTAACG CGGTATTTAC AACCGGTCAT GAAGTGGCTA      240

CTCTCTTTTG GGAGCGCTCC CGTGCCGCTA GTCACACTGG GACGTGAATG GCGTCACGGT      300

AGGGCTCGTC GTGTGACACG CATTTTCGAC CCTGCTTTAA GTCCCTAAGT GGGAGCGCTC      360

CCAGCCTTCG GGAGAACTCC CACACAACCA ACCGTCCGAC GCCACTCTCC CAGCGCTCAA      420

ACGGAGGCAG CAGTGTTCAC CATCCCCCGC TCCCCTCCGG GGCGCCCGGC CGTCGTCCGC     480

GCAACCACCC CGACCGGTCG GCTGAACACT GCAGCGTCCG GTTCTCGACC ATCCCCTTGC      540

GAGAGAACAT CCTCCAACCA AGGAAGACAC CGATATGAGT AAAGTTCGTG CCACGAACAG      600

ACGTTCGTGG ATGCGGCGCG GGCTGGCAGC CGCCTCTGGA CTGGCGCTTG GCGCCTCCAT      660

GGTGGCGTTC GCTGCTCCGG CCAACGCCGC CGGCTGCTCG GTGTACTACA CGGTCAACTC      720

CTGGGGTACC GGGTTCACCG CCAACGTCAC CATCACCAAC CTCGGCAGTG CGATCAACGG      780

CTGGACCCTG GAGTGGGACT TCCCCGGCAA CCAGCAGGTG ACCAACCTGT GGAACGGGAC      840

CTACACCCAG TCCGGGCAGC ACGTGTCGGT CAGCAACGCC CCGTACAACG CCTCCATCCC      900
```

-continued

```
GGCCAACGGA ACGGTTGAGT TCGGGTTCAA CGGCTCCTAC TCGGGCAGCA ACGACATCCC     960
CTCCTCCTTC AAGCTGAACG GGGTTACCTG CGACGGCTCG GACGACCCCG ACCCCGAGCC    1020
CAGCCCCTCC CCCAGCCCTT CCCCCAGCCC CACAGACCCG GATGAGCCGG GCGGCCCGAC    1080
CAACCCGCCC ACCAACCCCG GCGAGAAGGT CGACAACCCG TTCGAGGGCG CCAAGCTGTA    1140
CGTGAACCCG GTCTGGTCGG CCAAGGCCGC CGCTGAGCCG GGCGGTTCCG CGGTCGCCAA    1200
CGAGTCCACC GCTGTCTGGC TGGACCGTAT CGGCGGGATC GAGGGCAACG ACAGCCCGAC    1260
CACCGGCTCC ATGGGTCTGC GCGACCACCT GGAGGAGGCC GTCCGCCAGT CCGGTGGCGA    1320
CCCGCTGACC ATCCAGGTCG TCATCTACCA CCTGCCCGGC CGCGACTGCG CCGCGCTGGC    1380
CTCCAACGGT GAGCTGGGTC CGATGAACT CGACCGCTAC AAGAGCGAGT ACATCGACCC     1440
GATCGCCGAC ATCATGTGGG ACTTCGCAGA CTACGAGAAC CTGCGGATCG TCGCCATCAT    1500
CGAGATCGAC TCCCTGCCCA ACCTCGTCAC CAACGTGGGC GGGAACGGCG GCACCGAGCT    1560
CTGCGCCTAC ATGAAGCAGA ACGGCGGCTA CGTCAACGGT GTCGGCTACG CCCTCCGCAA    1620
GCTGGGCGAG ATCCCGAACG TCTACAACTA CATCGACGCC GCCCACCACG GCTGGATCGG    1680
CTGGGACTCC AACTTCGGCC CCTCGGTGGA CATCTTCTAC GAGGCCGCCA ACGCCTCCGG    1740
CTCCACCGTG GACTACGTGC ACGGCTTCAT CTCCAACACG GCCAACTACT CGGCCACTGT    1800
GGAGCCGTAC CTGGACGTCA ACGGCACCGT TAACGGCCAG CTCATCCGCC AGTCCAAGTG    1860
GGTTGACTGG AACCAGTACG TCGACGAGCT CTCCTTCGTC CAGGACCTGC GTCAGGCCCT    1920
GATCGCCAAG GGCTTCCGGT CCGACATCGG TATGCTCATC GACACCTCCC GCAACGGCTG    1980
GGGTGGCCCG AACCGTCCGA CCGGACCGAG CTCCTCCACC GACCTCAACA CCTACGTTGA    2040
CGAGAGCCGT ATCGACCGCC GTATCCACCC CGGTAACTGG TGCAACCAGG CCGGTGCGGG    2100
CCTCGGCGAG CGGCCCACGG TCAACCCGGC TCCCGGTGTT GACGCCTACG TCTGGGTGAA    2160
GCCCCCGGGT GAGTCCGACG GCGCCAGCGA GGAGATCCCG AACGACGAGG GCAAGGGCTT    2220
CGACCGCATG TGCGACCCGA CCTACCAGGG CAACGCCCGC AACGGCAACA ACCCCTCGGA    2280
TGCGCTGCCC AACGCCCCCA TCTCCGGCCA CTGGTTCTCT GCCCAGTTCC GCGAGCTGCT    2340
GGCCAACGCC TACCCGCCTC TGTAAAGCGG AGTGAGGCAA CGGCTGACAG CCTCAACGAG    2400
GAACTGATCA GCACCTCCTA GCCGGAGACG GCGCCCGTCC ACTCCCCGTG GGCGGGCGCC    2460
GCTTTTATGC CGACCCGTGC CCCAGCCGCA AGGGGCACGG GTCGGCCTAT TCCGGCGATG    2520
TCGGTCACGT CGCCCTAGCA CCCGGAAACG CCGAGAAAGA CTGCCCCGAA ACGGTCCTCT    2580
CCCATCCCTG CATTAGGTTG GCCGAGTCCG CCTATGGCTT CGTGGGCCGG AACCCAACCC    2640
ACCATCAACG AGAGGTATCA CCATGGCCAG TGTGGTGAAA TTCAATGTGC TGACGGTTCC    2700
TCCCGGTGCC GGCGCCACCC CGGAGGACGT TTGCCAAGCG CGCAGGCCTC GTGGAGAACC    2760
GGGCCGGGTT TCACGAGTTC CAACTGCCGG CGCCCGGCGA CGGGACGGAC AAGTACATCG    2820
TCTACACGCG CTGGCGCTCC GGAGAGGACT ACCAGAACTG GCTGAACAGC GAGGCCTTCC    2880
AGCGCGGACA CGCCCAGGCC TCTGAAGACT CCCGCCGCAG CAGCCAGGGC GGCCCGGCCG    2940
CGTCCGCGAG TGAACTCTGG TCCTTCGAAG TCGTCCAGCA CGTCCAGGCC CAGGACTGAT    3000
CCCGGTGCGG CCCTCGGTTC TTTACCGGGG CCGCCCACC CCCTTCATCC CTTTTCTTCT     3060
CCCCCGCACC CCTTTTGATC TGCAATGATG GAATTCGCGA TTCTTGAGAA GGCCGATCGT    3120
GTCCATGACC GCGCAGAAGG CAGGACGACC ACGCGTACCG GTCGACATCG AAGGAGTCAA    3180
CTGACAGTGG GGACTATCGC GGGGCTGATT GTCGCGCTGT CAGGCGTGGG GATGGTCTCG    3240
GCCAACGTGC TCCCGTGGGA ACCGTCGGAC CCGGCATCCG TGGTCCCCGC CACCTCGCAG    3300
```

```
GGCAGCAGTT CTCCCATGAC GCCGGAGCCC TCGCGTCCCC GGTACCCCCA CTCGTGCGCT      3360

CCGTGGTCGA AGAGGTGCCC AGCGCAAGCG GAGAACTGCG GGTCGTCGAA GGTGACGGGG      3420

AGGTCGTCGG CGAAGGCACG CTCCTGCGCT ACCTGGTGGA GGTCGAAGAA GGGCTTCCCG      3480

GAGACCCCGC CGACTTCGCT GCA                                              3503

(2) INFORMATION FOR SEQ ID NO:3:

(i) SEQUENCE CHARACTERISTICS:
         (A) LENGTH: 21 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
         (A) ORGANISM: VSP Leader Sequence (xi) SEQUENCE DESCRIPTION: SEQ ID NO:3:

Met Lys Leu Phe Val Phe Phe Val Ala Ala Val Val Leu Val Ala Trp
1               5                   10                  15

Pro Cys His Gly Ala
            20

(2) INFORMATION FOR SEQ ID NO:4:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Xba E2 PCR Primer (xi) SEQUENCE DESCRIPTION: SEQ ID NO:4:

GCTCTAGATG AATGATTCTC CGTTC                                            25

(2) INFORMATION FOR SEQ ID NO:5:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

TGACCGGCAG CAAAATG                                                     17

(2) INFORMATION FOR SEQ ID NO:6:
```

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

GCTCTAGATG GCCGGCTGCT CGGTG                                              25

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

GGAATTCTTA CAGAGGCGGG TAG                                                23
```